(12) United States Patent
De Beni et al.

(10) Patent No.: US 12,350,110 B2
(45) Date of Patent: Jul. 8, 2025

(54) METHOD FOR DRIVING AN ULTRASOUND PROBE, ULTRASOUND PROBE AND ULTRASOUND SYSTEM COMPRISING SAID ULTRASOUND PROBE

(71) Applicant: Esaote S.p.A., Genoa (IT)

(72) Inventors: Stefano De Beni, Genoa (IT); Marco Crocco, Ovada (IT); Claudio Fertino, Genoa (IT)

(73) Assignee: Esaote S.p.A., Genoa (IT)

( * ) Notice: Subject to any disclaimer, the term of this patent is extended or adjusted under 35 U.S.C. 154(b) by 120 days.

(21) Appl. No.: 18/112,370

(22) Filed: Feb. 21, 2023

(65) Prior Publication Data

US 2023/0263508 A1  Aug. 24, 2023

(30) Foreign Application Priority Data

Feb. 24, 2022 (EP) .................................... 22158476

(51) Int. Cl.
*A61B 8/00* (2006.01)
*A61B 90/94* (2016.01)

(52) U.S. Cl.
CPC ............ *A61B 8/585* (2013.01); *A61B 8/4254* (2013.01); *A61B 8/565* (2013.01); *A61B 90/94* (2016.02)

(58) Field of Classification Search
CPC ... A61B 8/4433; A61B 8/4438; A61B 8/4444; A61B 8/4472; A61B 8/4477; A61B 8/56; A61B 8/54; G01S 7/52096
See application file for complete search history.

(56) References Cited

U.S. PATENT DOCUMENTS

| | | | |
|---|---|---|---|
| 5,505,203 A * | 4/1996 | Deitrich | G01S 15/899 600/459 |
| 5,552,645 A | 9/1996 | Weng | |
| 2004/0002657 A1 | 1/2004 | Marian | |
| 2013/0053697 A1* | 2/2013 | Holl | A61B 8/4472 600/459 |
| 2014/0107487 A1 | 4/2014 | Kim | |
| 2016/0262726 A1* | 9/2016 | Yoon | A61B 8/463 |
| 2019/0059855 A1* | 2/2019 | Jin | A61B 8/4472 |
| 2019/0059856 A1* | 2/2019 | Jin | A61B 8/4477 |
| 2022/0202522 A1* | 6/2022 | Czupi | G08B 5/36 |
| 2023/0181159 A1* | 6/2023 | Kremsl | G06F 3/0346 600/459 |

FOREIGN PATENT DOCUMENTS

CN     113 040 813 A1     6/2021

OTHER PUBLICATIONS

European Search Report and Written Opinion dated Aug. 10, 2022, which issued in the corresponding European Patent Application No. EP 22158476.

\* cited by examiner

*Primary Examiner* — Carolyn A Pehlke
(74) *Attorney, Agent, or Firm* — Dickinson Wright PLLC

(57) ABSTRACT

A method for automatically detecting of the probe which is selected for the use by the user without manual commands by the user and comprising monitoring the operational status of the probe by discriminating between probe not in use and probe in use by sensing at least the motion of the probe and by setting automatically a probe in an active status if a motion of the probe is sensed and setting the probe in an inactive status if the probe is stationary.

16 Claims, 7 Drawing Sheets

METHOD FOR DRIVING AN ULTRASOUND PROBE, ULTRASOUND PROBE AND ULTRASOUND SYSTEM COMPRISING SAID ULTRASOUND PROBE

BACKGROUND OF THE INVENTION

Current ultrasound systems may be provided in combination with different kinds of ultrasound probes. Ultrasound imaging probes may show different shapes and sizes in relation to the different body parts or organs to be imaged. Some ultrasound probes are passed over the body surface and are identified as external probes, whereas others are inserted into the body through the body openings and are defined as endocavitary probes. Furthermore, there are also three most common types of ultrasound imaging probes: convex, linear, and phased array probes. These probes are differentiated one from the other relatively to their construction, the arrangement of the piezoelectric crystals forming the transducer elements of the transducer array of the probe, the aperture or footprint, and the frequencies of the ultrasound transmitted and received by the said probes.

In the convex probes, the piezoelectric transducer elements forming the array of transducer elements are arranged on a curved surface and the probe generates a beam which is suitable for in-depth examinations. The footprint, the frequency, and applications depend on whether the probe is configured for acquiring 2 or 3-dimensional images and the said frequencies are in the range between 2.5 MHz and 7.5 MHz. The phased array probes are provided with a small footprint and low central frequency of between 2 MHz and 6.5 MHz and these probes generates beams having a triangular shape. In linear array probes, the piezoelectric transducer elements forming the array of transducers is linear and generates a beam having a rectangular shape. The footprint, the frequency and application of transducers depend on whether image to be acquired is a 2D or 3D image. The center frequency of the transmitted beams may be within the range from 2.5 MHz to 12 MHz. A further kind of ultrasound imaging probe is known as pencil probe or CW Doppler probe and is used for measuring blood flows or blood sounds having a small footprint of the transmitted beam and being driven at frequencies between 3,5 to 8 MHz.

Further differences of probes may be dependent on the construction of the probe itself in relation to the layers forming the transmission and receipt window of the probe. These differences may consist in the different kind of materials of the layers and/or in the different position of the layers in relation to the transducer elements and may vary within the same kind of probe from producer to producer.

Convex probes are typically used for abdominal, transvaginal, trans-rectal examinations and also for organ diagnosis. Phased array probes are mostly used in cardiac examinations, trans-esophageal examinations, abdominal and brain examinations. Linear probes are applied for imaging in relation to vascular examination such as for example arterial carotids examinations and in imaging of the breast, thyroid, tendon, arthrogenous imaging, intra-operative imaging and laparoscopy imaging. Endocavitary probes are typically used for imaging of rectum and vagina. The above list of application comprises only some examples and is not to be considered exhaustive.

Typically, during an examination, there is the need to change the kind of probe frequently. The probes connected by the corresponding interfaces to the ultrasound imaging system are selected for being operative to scanning images by a dedicated button which may be a physical button, such as in the form of a knob or similar or a virtual button represented by an icon on a touch screen depending on the kind of user interface provided on the ultrasound system in use.

The above physical and manual physical operation is time consuming, in particular when a frequent probe change is needed, and necessitates the user to physically touch the selection organ such as the mechanical or virtual button. This action may be connected with problems relating to ensuring a sterile environment. Indeed when passing from one patient to another patient it might be necessary or advisable or imposed by sanitary rule to carry out a sonification and/or sterilization of the ultrasound scanner in relation to parts which might have come in physical contact with the patient or the user either directly or indirectly.

SUMMARY OF THE INVENTION

According to an aspect of the present invention, a method for automatically detecting of the probe which is select for the use by the user is provided which allows to avoid a direct physical contact between the user and probe selection organs on the ultrasound scanner.

According to a further aspect, which may be provided in combination with the said previous one, the method further comprises operations for simplifying the change of a probe to be connected to the ultrasound system.

According to a further aspect an ultrasound probe is provided which is configured to carry out the method according to embodiments herein.

According to still a further aspect an ultrasound imaging system is provided which operates in combination with the above probe for carrying out the methods according to embodiments herein.

In relation to the said first aspect, a method for driving an ultrasound probe, comprises: Monitoring the operational status of a probe by discriminating between probe not in use and probe in use by sensing at least the motion of the probe and by setting automatically a probe in an active status if a motion of the probe is sensed and setting the probe in an inactive status if the probe is not moving or stationary.

According to an embodiment, a probe, preferably each probe to be used in an examination alternatively one to the other, is provided with a motion sensor, which motion sensor generates different signals as a function of the status of motion of the probe.

An embodiment may provide to differentiate between a motion signal corresponding to a null signal when the probe is not displaced and a signal different from the null signal when the probe is displaced.

The signal corresponding to a status in which the probe is stationary, this means at rest or not displaced by the user, and the signal generated when the probe is displaced are used as control signals of a probe activation selector which automatically drives a selection circuit of an ultrasound scanner, which selection circuit sets the corresponding probe as the active probe for the ultrasound image acquisition scans.

In combination with one or more of the above disclosed embodiments, the method may further provide the operations of adding to the motion status signal a probe identification code which may be further combined with a data record comprising at least part, preferably all the probe configuration parameters relating to the parameters necessary for correctly driving the probe for carrying out ultrasound imaging scans.

The setting of these parameters is necessary when operatively connecting a probe to an ultrasound system for allowing a correct driving of the probe for generating the transmitted beams and for receiving the reflected beams correctly according to a certain imaging mode.

Two variant embodiments may be possible which can be provided in parallel and may be selectable either manually or automatically when connecting a probe to an ultrasound system.

In the first embodiment, the method provides to store the said setting data record and to transmit the value of the setting of the parameters of the said setting data record to the ultrasound system with or without the identification code.

In the second embodiment, the setting data record is stored in a memory of the ultrasound system and is loaded and read by the ultrasound system control unit when the probe is connected to the ultrasound system and the probe identification code is sent to the probe selection circuit and/or is read by the said probe selection circuit.

According to a further improvement, in addition to sensing the condition of motion of a probe and providing signals indicative of said conditions of motion, a further step of sensing the orientation in space of the probe may be provided.

The orientation in space of the probe may be further used as a criterion for determining the operative status of the probe and specifically if the probe is in use or not in use, particularly if the probe is in a stand-by or parking position at a probe stand of the ultrasound system.

Thus, the probe may generate signals describing two conditions which can be used to discriminate its operative or stand-by condition relating, on one hand, to the motion of the probe due to displacements of the probe and, on the other hand, to indication of the spatial orientation of the probe.

Spatial orientation of the probe may be a discriminating parameter, since usually probes, which are connected to an interface of the ultrasound system, but are not in use or are in stand-by condition, are housed in a probe stand associated to the ultrasound system in which the probe is positioned with the transmission window of the probe oriented upwards, so that this condition may be used for discriminating if the probe is in an operative condition and has to be selected as active or if the probe is in a stand by or parking position and should be selected as inactive.

In relation to the second aspect of the present invention, an ultrasound probe is provided which is combined with one or more sensors measuring the displacement of the probe, the sensors having an output for signals indicating motion conditions of the probe, i.e. if the probe is stationary or stands still or if the probe is subject to displacements, the said signals having a predetermined structural configuration for representing univocally at least a condition of stationary or not moving probe and a condition of probe being in motion or displaced.

According to a further feature a memory may be provided in which a probe identification code which is characteristic for a specific probe is stored or may be stored and a combination section to which the said memory and the probe motion sensor are connected which combination section combines the said probe identification code to the signal indicating the condition of motion of the probe.

According to a further feature which can be provided in any combination with the previous disclosed features of the second aspect of the invention, the probe may be provided also with a memory in which setting data of setting parameters characteristic for the corresponding probe are stored and which setting data are configured according to a predetermined data structure and in order to be readable by a receiving unit, the data of the said record being fed to the combination unit and combined to the identification code of the probe and optionally to the signals indicating the condition of motion of the probe.

According to the third embodiment, the present invention is directed to an ultrasound system comprising at least one probe connected to a probe communication interface of the said ultrasound system or to a combination of an ultrasound system having connection interfaces for communication with at least one probe and of at least one probe having a communication interface connectable or connected to the corresponding communication interface of the ultrasound system, the said probe being configured according to one or more of the embodiments described above and/or showing one or more of the features of the said embodiments, the said ultrasound system, comprising a probe selection circuit, with an input for the signals indicating the motion condition of the probe and/or for the signals indicating the spatial orientation of the probe and a processing unit generating a probe activation signal or a probe deactivation signal as a function of the said signals indicating the probe motion condition and/or the probe orientation and transmitted by the probe.

According to a further embodiment the probe selection circuit may be provided in combination with signaling means generating visual information relating to one or more of the following conditions: probes connected to the ultrasound system and being activable for use; probe currently activated.

According to a further embodiment, the ultrasound system is further provided with a database of data records comprising setting values of configuration parameters for driving a corresponding probe, the said database being stored in a probe memory and the record relating to the values of the setting parameters for each corresponding probe being univocally related to a probe identification code, the said selection circuit receiving the said probe identification code forma probe connected to the ultrasound system and automatically addressing the setting data record of the probe corresponding to the said probe identification code, the said probe selection circuit automatically being connected to the ultrasound system control processor and transmitting to the said control processor the probe setting data corresponding to the probe identification code for configuring the ultrasound system to correctly drive the said probe.

According to a further feature, the selection circuit is configured to generate a list of different probes connected to the ultrasound system and alternatively to address the probe setup data record corresponding to the probe identification code for which the motion indication and/or the orientation signals correspond to an activation condition and the said selection circuit transmits the said probe setting data relating to the probe to be activated to the ultrasound system control processor for correct configuration of the system for driving the said probe.

According to still a further feature, a combination of one ultrasound system and at least two different probes is provided, each probe being configured according to one or more of the preceding embodiments and each probe being connected to a communication interface with the ultrasound system, the ultrasound system being provided with a probe stand for supporting the probes not in use in a stand by or rest condition, the said probes having a specific orientation when positioned on the said stand, the ultrasound system being provided with a selection circuit communicating with the probes and comprising a memory for storing identification codes of each probe and/or setting data records of the ultrasound system for driving each of the said probes, the said selection circuit receiving from each probe signals indicating the motion condition of the corresponding probe and/or signals indicating the orientation of the said probes, the said signals triggering the activation of a probe when said signals corresponds to an indication of motion of the probe and/or to an indication of change in the orientation of the probe.

The said setting data records of the parameters for driving a certain specific probe are transmitted by the corresponding probe at least for a part of them to the selecting circuit or the said setting data records of the parameters for driving the said probe being at least for a part of them stored already in a memory of the setting circuit.

In an embodiment the communication interface of the ultrasound system with the probes are activated alternatively one from the other by the selection circuit for the corresponding displaced and/or differently oriented probe.

Activation of the said communication interfaces may consist in allowing the communication with the corresponding probe or in connecting the corresponding probe interface of the ultrasound system with the channels feeding the driving signals to the transducer elements of the transducer array of a probe and the channels for feeding the receive signals generated by the reflected ultrasound beams falling onto the transducer elements to the processing channels of the ultrasound scanner.

Further embodiments of the present invention are disclosed in the following description and are subject of the dependent claims.

In the above embodiments, the sensor associated to each probe for sensing the condition of motion of the probe and/or the orientation in space may be of different kind and in a particular embodiment the said sensors may consist in one or more accelerometers and/or one or more gyroscopes and/or combinations thereof.

Furthermore, specific forms of the signals can be determined which are related in relation to the form of the signal and in relation to the signal amplitude and/or intensity to particular and typical movements of the probe for being used. A particular movement may be the characteristic pick up movement of the probe from a probe supporting stand. The characteristic of this signal may be determined by experiments. Many pickup actions may be carried out and the corresponding signals form the sensors may be registered. An average of the registered signals may be calculated in order to define certain statistics and or tolerances. The said signal form related to the said characteristic movements of the probe may be stored in a memory and the activation may be triggered by a comparator provided in the selection circuit when the signals indicating the condition of motion of a probe received by the selection circuit corresponds within the said tolerances to the saved experimentally determined reference signal. also the signal indicating that the probe is at rest or not used can subjected to a similar process, determining its form in an experimental way and saving the results as a reference signal and comparing the signals received by the probe with the said reference signal.

The above process may be simplified by considering only signal intensity and not the waveform of the signal as in the previous embodiment. In this case a threshold may be set for a reference intensity and when the intensity of signal indicating the motion condition and/or the orientation coming from a probe is above of the said threshold the activation of the said probe is triggered while when the signals indicating the condition of motion and/or the orientation of the probe are below the said threshold the probe is maintained inactive or commuted in the inactive condition.

Further discrimination algorithm may be used for evaluating if a probe is to be activated or deactivated as a function of the signals indicating the condition of motion and/or the orientation of the said probe.

The above embodiments not only allow to easily and automatically activate and deactivate respectively probes which are taken in use by the user and probes which are put in stand-by condition, but when the orientation of the probe is considered, the deactivation provides for limiting the heating of the probe due to deactivation of the transducer elements of the said probe.

Furthermore, by providing the probes and/or the ultrasound system with setup data for each different kind of probes in order to allow the ultrasound system to correctly drive a certain probe, the setup of the system is simplified and can be more rapidly carried out. This results also in more rapid upgrade of the system to new configurations of the probes, which can provide for an automatic configuration of the ultrasound system in relation to the settings for driving the said new probe.

BRIEF DESCRIPTION OF THE DRAWINGS

Exemplary embodiments of the present invention are disclosed in the following and with reference to the annexed figures in which:

FIG. 1 illustrates a high-level block diagram of an ultrasound system implemented in accordance with embodiments herein. Portions of the system (as defined by various functional blocks) may be implemented with dedicated hardware, analog and/or digital circuitry, and/or one or more processors operating program instructions stored in memory. Additionally or alternatively, all or portions of the system may be implemented utilizing digital components, digital signal processors (DSPs) and/or field programmable gate arrays (FPGAs) and the like. The blocks/modules illustrated in FIG. 1 can be implemented with dedicated hardware (DPSs, FPGAs, memories) and/or in software with one or more processors.

Figure 1:
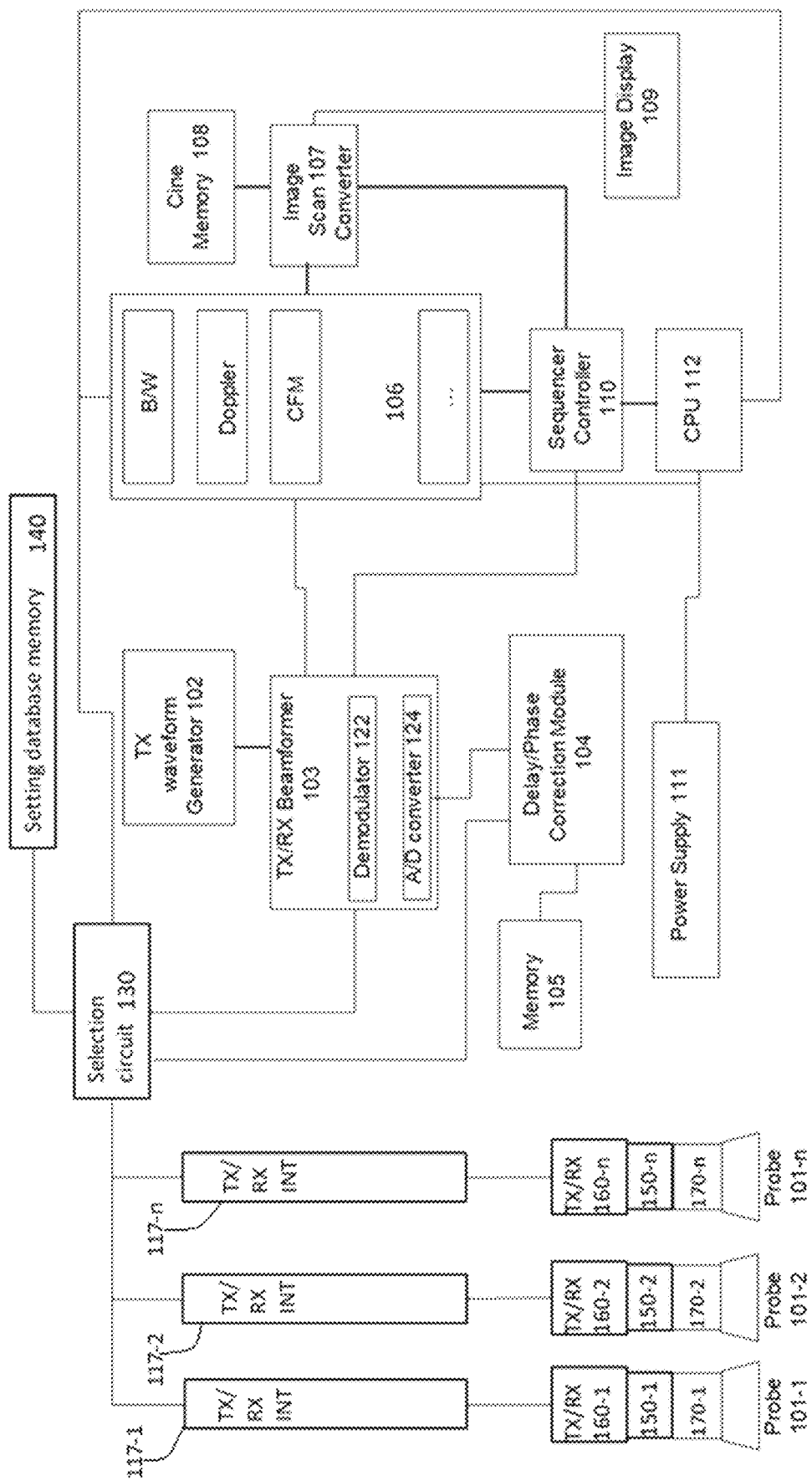
FIG. 1 is a high-level block diagram of an embodiment of a system according to the present invention.

The ultrasound system of FIG. 1 includes one or more ultrasound probes indicated respectively 101-1, 101-..., 101-n with n a natural number. Each probe 101-1, 101-2, ..., 101-n may include each one a different kind of various transducer array configurations, such as a one dimensional array, a two dimensional array, a linear array, a convex array and the like. The transducers of the array may be managed to operate as a 1D array, 1.25D array, 1.5D array, 1.75D array, 2D array, 3D array, 4D array, etc. The probes may be of any one of the different kinds as described in the previous description.

Each of the ultrasound probes 101-1, 101-2, ..., 101-n is coupled over a wired or wireless link to a dedicated transmitting/receiving interface 117-1, 117-2, ..., 117-n of an ultrasound system. Each probe 101-1, 101-2, 101-*n* is provided with a corresponding transmitting/receiving interface 160-1, 160-2, 160-*nn*.

In relation to the above term transmitting/receiving interface of the ultrasound system and of the probes this term is used in the present disclosure and in the claims in such a way as comprising not only the circuits for coding and formatting the signals exchanged by the probes and the ultrasound system, but also the physical connection devices, such as the cables and the connectors and/or in the case of a wireless connection the circuits setting up the transmission protocols of the corresponding wireless communication system in use.

Differently from traditional ultrasound systems according to the state of the art the probes are not directly connected to a beamformer unit such as the beamformer 103 but a selection circuit 130 is provided which connects alternatively one of the probes 101-1, 101-2, 101-*n* to the transmit/receive beamformer 103 and to the signal processing channels. According to the specific exemplary embodiment of FIG. 1, the beamformer 103 includes a transmit (TX) beamformer and a receive (RX) beamformer that are jointly represented by TX/RX beamformer 103. The TX and RX portions of the beamformer may be implemented together or separately. The beamformer 103 supplies transmit signals to the probe 101 and performs beamforming of "echo" receive signals that are received by the probe 101.

A TX waveform generator 102 is coupled to the beamformer 103 and generates the transmit signals that are supplied from the beamformer 103 to the probe 101. The transmit signals may represent various types of ultrasound TX signals such as used in connection with B-mode imaging, Doppler imaging, color Doppler imaging, pulse-inversion transmit techniques, contrast-based imaging, M-mode imaging and the like. Additionally, or alternatively, the transmit signals may include single or multi-line transmit, shear wave transmit signals and the like.

The beamformer 103 performs beamforming upon received echo signals to form beamformed echo signals in connection pixel locations distributed across the region of interest. For example, in accordance with certain embodiments, the transducer elements generate raw analog receive signals that are supplied to the beamformer. The beamformer adjusts the delays to focus the receive signal along one or more select receive beams and at one or more select depths within the region of interest (ROI). The beamformer adjusts the weighting of the receive signals to obtain a desired apodization and profile. The beamformer applies weights and delays to the receive signals from individual corresponding transducers of the probe. The delayed, weighted receive signals are then summed to form a coherent receive signals.

According to the present exemplary embodiment, the beamformer 103 includes (or is coupled to) an A/D converter 124 that digitizes the receive signals at a select sampling rate. The digitization process may be performed before or after the summing operation that produces the coherent receive signals. The beamformer also includes (or is coupled to) a demodulator 122 that demodulates the receive signals to remove the carrier waveform. The demodulation may be performed before or after the summing operation. Once the receive signals are demodulated and digitized, complex receive signals are generated that include I, Q components (also referred to as I, Q data pairs). The I, Q data pairs are saved as image pixels in memory. The I, Q data pairs, defining the image pixels for corresponding individual locations along corresponding lines of sight (LOS) or view lines. A collection of image pixels (e.g., I, Q data pairs) are collected over time and saved as 2D image frames and/or 3D volumes of image data. The image pixels correspond to tissue and other anatomy within the ROI.

A dedicated sequencer/timing controller 110 may be programmed to manage acquisition timing which can be generalized as a sequence of firings aimed at selecting reflection points/targets in the ROI. The sequence controller 110 manages operation of the TX/RX beamformer 103 in connection with transmitting ultrasound beams and measuring image pixels at individual LOS locations along the lines of sight. The sequence controller 110 also manages collection of receive signals.

One or more processors 106 perform various processing operations as described herein.

In accordance with embodiments herein, the beamformer 103 includes an input that configured to be coupled to an ultrasound probe 101 and receive signals from transducers of the ultrasound probe 101. The demodulator 122 demodulates the receive signals to generate complex receive signals by removing the carrier from the receive signal. The memory 105 stores time delays to align contributions of reflection signals received by the transducers of the array of the probe 101. The memory 105 also stores phase corrections to correct phase differences introduced by the time delays.

A delay/phase correction (DPC) module 104 is coupled to the memory 105 and provides various delays and corrections (e.g., coarse, fine, etc.) to the beamformer 103. For example, the DPC module 104 directs the beamformer 103 to apply time delay and phase correction to the complex receive signals to form delayed complex receive signals. The beamformer 103 then sums, in a coherent manner, the delayed complex received signals to obtain a coherent receive signal in connection with a reflection point or a reflection target.

A memory 105 may store coarse corrections calculated as a multiple of a sampling time. A common coarse correction may be stored in connection with multiple channels. Alternatively, different coarse corrections may be stored in connection with various corresponding channels. The memory 105 may also store fine corrections calculated as a fraction of the sampling time. Different fine corrections are be stored in connection with various corresponding channels based on the calculations described herein. As explained herein, the beamformer 103 (circuitry) is configured to apply the coarse and fine corrections contemporaneously by multiplying the complex receive signals by a complex carrier delayed by the multiple of the sampling time and by the fraction of the sampling time.

The memory 105 may store a pre-calculated table, where the pre-calculated table comprises real times of arrival of the receive signals relative to a predetermined reflection point. Optionally, the processor 106 may be configured to calculate real times of arrival of the receive signals relative to a predetermined reflection point. The processor 106 may be configured to calculate the coarse delay for baseband signal components of the complex receive signals, in connection with a plurality of channels, by a round function of real times of arrival associated with each of the channels. The processor 106 may be configured to calculate a fractional value of the fine correction based on real times of arrival for a plurality of channels.

The beamformer 103 circuitry may further comprise a complex multiplier configured to multiply the fractional value by the complex receive signal for the corresponding channel to which the corresponding coarse correction has been added.

In accordance with certain embodiments, at least a portion of the beamforming process may be implemented by the processor 106 (e.g., in connection with software based beamforming). For example, the memory 105 may store beamforming related program instructions that are implemented by the processor 106 to apply fine and coarse corrections to the complex receive signals.

The processor 106 may be configured to provide parallel multi-line receive (PMR) fine correction in baseband in connection with individual view lines acquired in parallel contemporaneously with a focusing function.

The processor 106 and/or CPU 112 also performs conventional ultrasound operations. For example, the processor 106 executes a B/W module to generate B-mode images. The processor 106 and/or CPU 112 executes a Doppler module to generate Doppler images. The processor executes a Color flow module (CFM) to generate color flow images. The processor 106 and/or CPU 112 may implement additional ultrasound imaging and measurement operations. Optionally, the processor 106 and/or CPU 112 may filter the first and second displacements to eliminate movement-related artifacts.

The processor and/or CPU 112 may be also configured to setup the transmitted and/or received ultrasound beams in order to cover alternatively a high-depth and large field of view scan of the target region and a zoomed scan of a limited zone of the said target region. The settings may be saved in the memory 105. The sequence controller 110 may be configured or driven to control the ultrasound system for carrying out in an interlaced manner an ultrasound scan for acquiring a high-depth and large FoV image and a zoomed image as defined above and according to the setup of the parameters settings for the beamformers saved in the memory 105.

An image scan converter 107 performs scan conversion on the image pixels to convert the format of the image pixels from the coordinate system of the ultrasound acquisition signal path (e.g., the beamformer, etc.) and the coordinate system of the display. For example, the scan converter 107 may convert the image pixels from polar coordinates to Cartesian coordinates for image frames.

The output of the Image scan converter 107 is then displayed on the display 109. This display is in the present embodiment the display of the ultrasound scanner but more displays may be provided at least one of which is a display of the separate image processing device or of a separate image displaying station which may be also provided at remote site relatively to the site at which the ultrasound system is located.

Returning back to the selection circuit 130, this circuit can be configured according to different alternatives each one providing a combination of different functions.

FIG. 1 shows a hardware configuration which is the most complete one. The main function of the selection circuit is to connect the TX7RX interface 117-1, or 117-2 or 117-*n* to the TX/RX beamformer 103 depending on the operating status of a corresponding probe 101-1, 101-2, 101-*n*. With operating status according to the present invention, it is meant a condition of motion and/or displacement of a probe which is characteristic of the manipulation of the probe for carrying out a certain examination and/or at least the pick up of the probe from a stand at which the probe is temporarily secured when not in use. In addition or alternatively the said operative condition may also be the condition in which the probe is displaced in such a way that the orientation in space of the probe is changed from a characteristic orientation which the probe has when in stand-by or not in use, for example at the probe stand and a characteristic orientation of the probe when ready to be used for carrying out an imaging scan.

The selection circuit operates in such a way as to activate the one of a certain number of probes 101-1, 102-1, 101-*n* connected to the ultrasound system for which the displacement of the corresponding probe 101-1, or 101-2 or 101-*n* and/or a change in orientation of the said corresponding probe is detected by one or more of the sensors 150-1, 150-2, 150-*n* associated to the respective probe.

Many different kinds of sensors can be used for determining the condition of motion and/or of orientation in space of each probe. According to an embodiment, at least one accelerometer or a gyroscope or a combination of the said one may be used or a combination of one or more accelerometers and/or of one or more gyroscopes may be used.

Signals coming from the said sensors 150-1 or 150-2 or 150-*n* of a corresponding probe 101-1, 101-2, 101-*n* which has been grasped and manipulated by the user are fed to the selection circuit. This circuit may be configured to receive signals transmitted by the sensor/sensors of a probe and to analyze the said signals in order to determine if the signals have to be interpreted as signals indicating a condition of motion and a condition of change in orientation of a probe. If this is the case the selection circuit is configured to activate the connection of the corresponding probe with the beamformer 103, with the ultrasound receive signals processing channels of the ultrasound scanner and with the further processing circuit generating an image out of the said signals.

According to an embodiment, each probe 101-1, 101-2, 101-*n* or at least some of the probes may also be provided with an onboard memory 170-1, 170-2, 170-*n* in which an exclusive identification code is saved. The TX/RX interface 160-1, 160-2, 160-*n* of the corresponding probe 101-1, 101-2, 101-*n* may be configured to add the said probe identification code to the signals provided by the motion condition and/or orientation measuring sensor/sensors 150-1, 150-2, 150-*n* of the corresponding probe.

According to a variant embodiment which is not shown in detail, each probe, or at least one of the probes may be provided with a signal processor which is configured to generate a message according to a communication protocol in which the identification code and the signal or the signals generated by the sensor or by the sensors are packaged.

Many variant embodiments may be used for this kind of message structure for coding in it the said identification code and the signal or the signals generated by the sensor or by the sensors and the skilled person may choose the most appropriate one from the message structures and the data message transmission protocols known at the state of the art. For example, a typical serial bus communication protocol can be used or a parallel bus transmission protocol may be used or other communication protocols known at the state of the art.

The selection circuit 130 is configured to unpack the messages and extract the identification code of the transmitting probe and also extract the signals of the sensor or of the sensors and analyze them.

According to a further improvement a memory 140 may be provided in the ultrasound scanner in which setting data of the ultrasound system circuits are stored for correctly setting the said ultrasound system for driving a certain probe. The said setting data may be in the form of a setting data database and the setting data for each different probe may be associated to the exclusive probe identification code of a corresponding probe kind.

The setting information for the ultrasound system needed to set the system for correctly driving a certain probe may be provided at the production site or may be loaded, later on, when a probe is connected for the first time to the system. This can be done according to installation processes which are currently used for the installation of the drivers of peripherals of personal computers or similar devices.

In a possible and only exemplary embodiment, when connecting for the first time a probe to an ultrasound system, the system first of all automatically receives the probe identification code from the probe or automatically addresses the memory 170-1, 170-2 or 170-$n$ of a corresponding probe to read the said identification code. A scanning of the database saved in memory 140 is carried out for looking of a corresponding probe identification code and if such a code is found, the installation of the probe is considered completed. A buffer or temporary memory may be provided in which the setting data for the connected probe are temporarily stored in a ready to use condition, the said setting data corresponding to the identification code of the probe being copied from the setting database memory 140 to the temporary buffer memory 105.

If the scanning of the setting database reveals that no setting data is provided in it for the identification code corresponding to the newly connected probe to the ultrasound scanner, a loading cycle of the said setting data and the storing of the said setting data in the setting database memory 140 may be carried out as well as the loading of the said setting data into the temporary buffer memory in a ready to use condition.

The said setting data may be provided in a memory such as the memory 170-1, 170-2, 170-$n$ of the corresponding probe 101-1, 101-2, 101-$n$ so that the setting circuit 130 reads the setting data from the said memory and carry out the steps of storing the said setting data in the setting database memory 140.

Alternatively, or in combination the complete set of setting data or at least part of it may be downloaded by a remote server for example of the probe producer. When determining that the setting data of the probe of which the identification code has been read are not present in the setting database memory 140, the selection circuit 130, may trigger the communication peripherals of the ultrasound system to connect to the site of the probe producer and automatically download the setting data relating to the probe having the identification code read by the setting circuit 130.

As a further variant embodiment, the setting circuit may directly transmit and load the setting data to the different control circuits and processors of the ultrasound scanners for configuring the said control circuits and/or processors to carry out the relating functions in an harmonized way with the probe in use. So, for example, but in a nonlimiting way, the setting data are transmitted to the processor 106, to the CPU 112, to the Transmit and receive beamformer 103 and to the demodulator 122 and the A/D converter 124.

In a variant embodiment, the said installation process of a new probe may be carried automatically by the probe itself or partially by the probe and partially by the setting circuit of the ultrasound system. In this variant embodiment, when connecting a probe to the ultrasound system to a transmission/receiving interface not in use by a probe, the probe sends the identification code to the setting circuit 130. This setting circuit is configured to verify if the identification code is present in the database in the memory 140. If it is present the setting unit 130 send an "end" signal to the probe for ending the installation process. If the code is not present the selecting circuit 130 sends a "go on" signal to the probe which begins the download in the memory 140 of the setting data relating to the said probe.

The functions described above in each of the different variant embodiments may be incorporated in the configuration of the electronic circuits of the probe and/or of the selecting circuit 130. According however to a preferred embodiment the said functions may be in the form of a software program in which the instructions are coded for configuring a conventional processing hardware and/or the relating peripherals to carry out the said functions and processing steps described above.

The hardware of the selecting circuit and/or of the memories 140, 105, 170-1, 170-2, 170-$n$ and of the other operative units of the probes and of the ultrasound system being a generic processing hardware which loads and executes the said software or at least a part of it. Part of the software may be executed by the hardware onboard of the probes and part by the hardware forming the selecting circuit 130.

In relation to the steps of analyzing the signals provided by the sensor or by the sensors onboard of the probes, different kind of signal analysis may be carried out and different criteria for discriminating if a probe has been subjected to displacement and/or change of orientation or not may be used.

A first basic process of the signal or signals generated by the sensors may be a simple determination of a maximum or minimum signal peak or an average maximum or an average minimum signal peak over a certain time window and the comparison with the said maximum peak or the said minimum peak with a threshold value. This value may be related to the amplitude of the signals. Depending on whether the signal peak is above or below the said threshold value the signals are interpreted as relating to a condition of displacement of the probe and/or a condition of change in orientation.

In this case, the selecting circuit may be provided with a comparator section which compares the amplitude peaks with the reference threshold and causes the triggering of the activation of a probe as a function of the said comparison by generating an activation signal to be fed to the operative units of the ultrasound scanner.

Alternatively or in combination a more precise signal analysis may be carried out which is related to the signal frequency spectrum and/or also to the signal waveform. In this case a signal pattern may be generated by experiments for determining a signal pattern (amplitude, waveform and/or frequency spectrum) which is characteristic of typical displacement to which a probe is subjected when being manipulated by a user. In particular, since automatic activation of a probe is desired the empirically determined signal pattern may be determined in relation to the picking up of a probe from a probe stand in which the probes are positioned when not in use.

Recording the signals generated for a certain number of picking up actions on the same probe a statistically valid reference signal pattern is determined which can also be associated to a tolerance within which a measured signal coming from an identical probe being picked up during normal use may be considered identical to the reference signal and the displacement of the probe is interpreted as being a pick up action of the probe so that the selecting circuit 130 triggers the activation of the corresponding probe.

According to the above example, activation not only means activating the connection of the probe with the processing channels of the ultrasound system, as described above or according to other variant embodiment of the ultrasound system processing unit, but also optionally means loading in the processors and control units and in the beamformer of the ultrasound system the setting data for configuring the said units to operate correctly the connected and activated probe.

In relation to this embodiment, the selecting circuit 130 may be provided with signal processing unit which is configured to carry out a signal pattern comparison using different algorithms, such as for example cross-correlation algorithms, minimization of cost functions or others. The said The instructions for configuring the processing unit provided in the selection circuit 130 or associated to it may to carry out the said comparison algorithms are coded in a software which is loaded and executed by the processing unit. A driving signal triggering the activation of the corresponding probe is then generated as a function of the result of the said comparison of the signal pattern resulting from the measurement by the sensors and the pattern of the reference signal.

Figure 2:
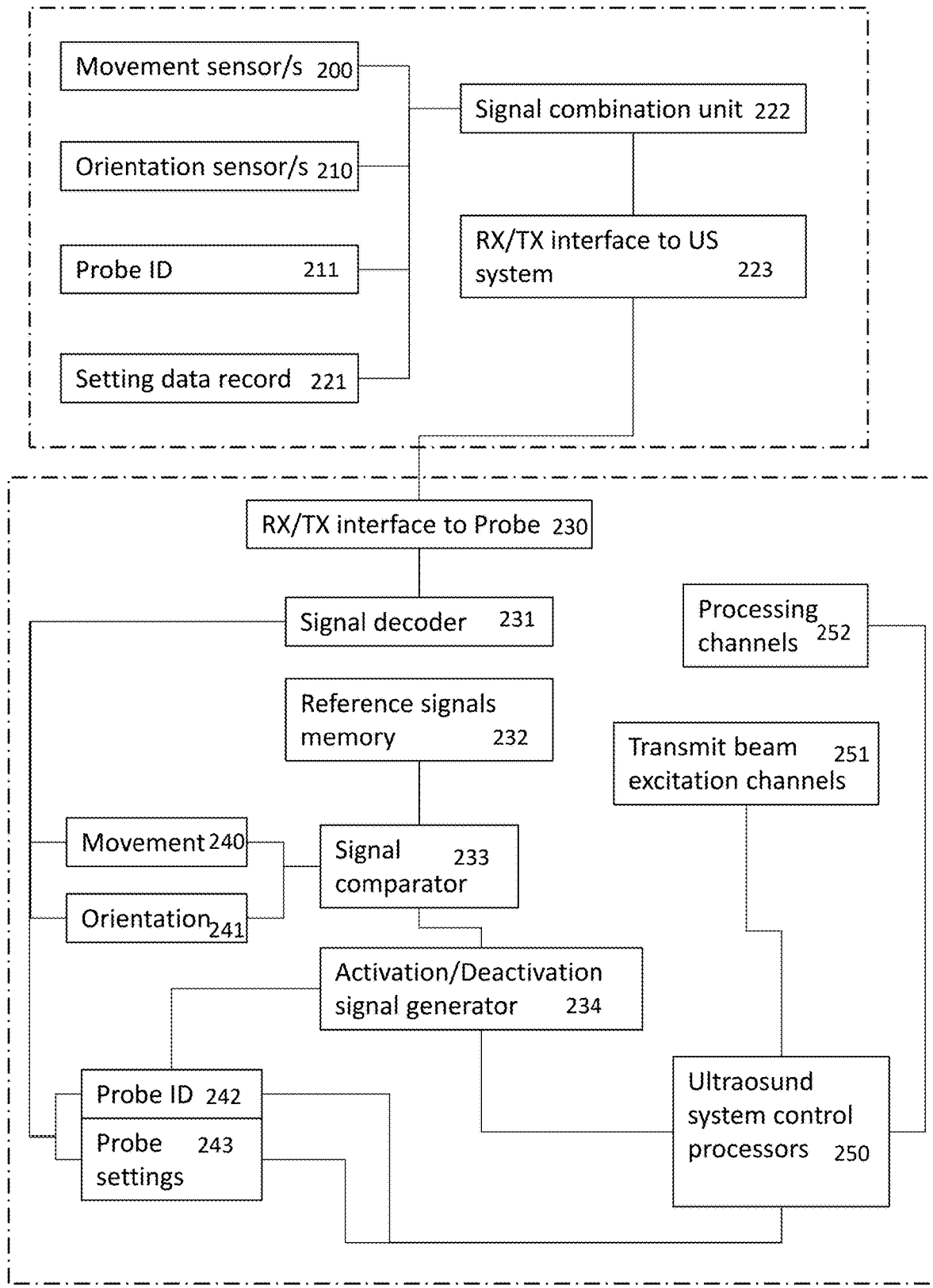
FIG. 2 is a bock diagram of a further embodiment of the present invention.

FIG. 2 shows a block diagram of a more detailed embodiment of a probe and a selecting circuit according to an embodiment of the present invention.

The probe indicated by 101 comprises one or more movement sensors detecting the motion condition of the probe and indicated by 200. Furthermore, the probe 101 is also provided with one or more orientation sensors indicated by 210. In a memory 211 a specific and exclusive probe identification code is stored and can be read from the memory or is transmitted by the memory 211. In a memory 221 of the probe 101 there is stored a setting data record, comprising the values to be set for different configuring parameters of the ultrasound scanner in order for the ultrasound system to correctly drive the probe 101. The output of the sensors 200 and 210 and of the memory 211 and 221 are fed or are read from a signal combination unit 222 which generates structured data messages according to predefined transmission protocols which are shared with the ultrasound scanner selection circuit 130 in order to extract the measured signals, the identification code of the probe and the setting data record. The probe 101 communicates by means of a transmitting/receiving communication interface 223 with the transmitting/receiving communication interface 230 of the ultrasound scanner, for example of the selecting circuit 230.

A signal decoder 231 unpacks the messages received from the probe 101 read extracts the measurement signals relating to the movements of the probe indicated by 240, the signals measured by the corresponding sensors relating to the orientation of the probe indicated by 241, the probe identification code 242 and the setting data for configuring the ultrasound system to correctly drive the probe and indicated by 243.

The said signals 240 and 241 relating to the measured displacements and/or orientation of the probe are processed by a signal comparator 233. This signal comparator may be configured according to one or more of the embodiments disclosed above. This comparator may be in the form of generic processing hardware executing a software in which the instructions are loaded for carrying out one or more signal comparation algorithms. The comparation is carried out with a reference signal stored in a memory 232 connected to the comparator 233. The reference signal may have one or more different forms depending from the kind of comparison algorithm and process selected and which process can be selected among the previously described ones or can be also a combination thereof.

Depending on the result of the comparison process the comparator 233 triggers a signal generator 234 to generate either an activation signal or no signal or also a deactivation signal.

In relation to the deactivation signal this signal may be generated when the measured data from the sensor or the sensors reveal that the probe is motionless or has a certain orientation which is typical for a stand-by or rest condition or not in use condition.

This deactivation signal may be also generated if the said signals relating to a condition of stationary or motionless probe or of a probe in an orientation typical for the said rest condition lasts for a predetermined time, after which the probe can be considered motionless or definitively oriented in a rest position.

The signal generator transmits the activation/deactivation signal to one or more control processors of the ultrasound scanners indicated globally with 250 and which may also comprise a control processor integrated in the selecting circuit 130. This determined the transmission of the probe ID data and of the probe settings 242 and 243 to the ultrasound system control processors 250 and the setting of the transmit beams excitation channels 251 and of the receive beams processing channels 252.

Although in the present example of FIG. 2 only the configuration and the activation of the transmit beam excitation channels and of the receive beams processing channels is disclosed in an explicit way, it is clear that the activation and the deactivation signals may determine the activation and the loading of the setting data of every control and processing circuit provided in the ultrasound system and taking part to the imaging acquisition process of the ultrasound system from the generation of the transmit beams to the display of an image according to one or more imaging modes. It is immediately clear for every skilled person which units or circuits has to be activated or deactivated and which setting data is to be loaded in which circuit.

Figure 3:
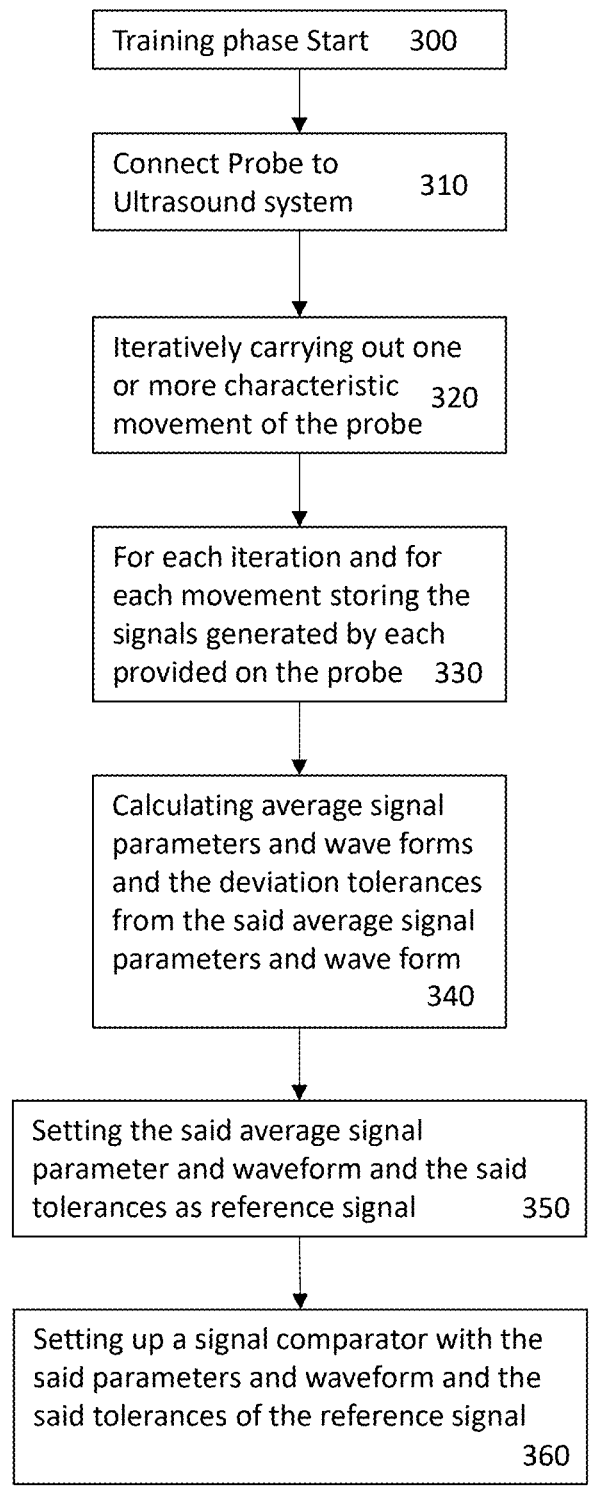
FIGS. 3 and 4 illustrates flow diagrams relating to embodiments respectively of a training phase and of the normal operative phase of the method according to the present invention.

FIG. 3 is a flow diagram illustrating an embodiment relating to the steps of a training phase of the comparator for determining a reference signal pattern, i.e. for example a combination of one or more of the parameters relating to signal amplitude peaks, signal waveform and/or signal frequency range. At step 300 a specific start command is inputted to the system. At step 310 a specific probe is connected to the ultrasound system and activated, for example by a manual command of the selection circuit 130.

At step 320, the user iteratively, i.e. repeatedly executes the movement of the probe which he carries out during executing of typical probe manipulation steps. In this case a preferred movement is the movement to which the probe is subjected during pick-up of the probe from a probe stand at which the probes are secure temporarily during stand-by or non-use.

A recording step 330 of the signal or the signals relating to the pick-up action of the probe and to motion and orientation variation of the probe are recorded and sored in a memory for further processing.

Step 340 provides for averaging the parameters defining the signal pattern, for example the combination of one or more parameters such as signal amplitude peaks, signal waveform and/or signal frequency range. Furthermore, optionally tolerances of the difference from the said averaged signal pattern are calculated with different statistical means such as for example standard deviation or other algorithms.

The said averaged signal pattern according to the above definition of pattern, is set as a reference signal for the comparison with measured signals. Also the tolerances are stored as disclosed at step 350.

The said reference signal and the said tolerances are used for the setting of a signal comparator which may be in the form of an algorithm able to compare simple numerical values of parameters and waveforms and/or frequency ranges such as for example a cross correlation algorithm or similar algorithms as indicated by step 360.

This last step ends the training phase of the selection circuit for a specific probe and has to be repeated, preferably, for every different probe.

Figure 4:
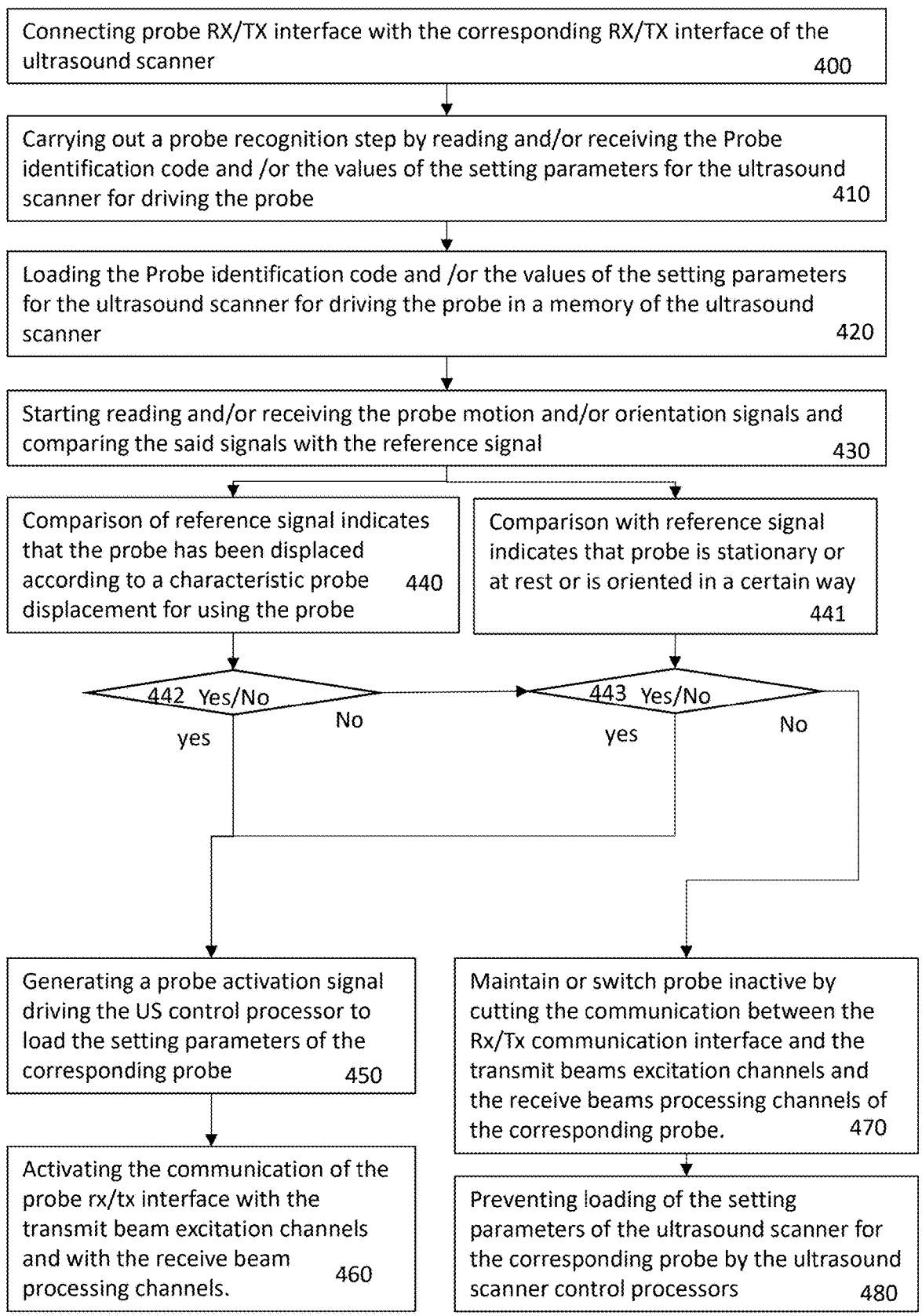
Figure 5:
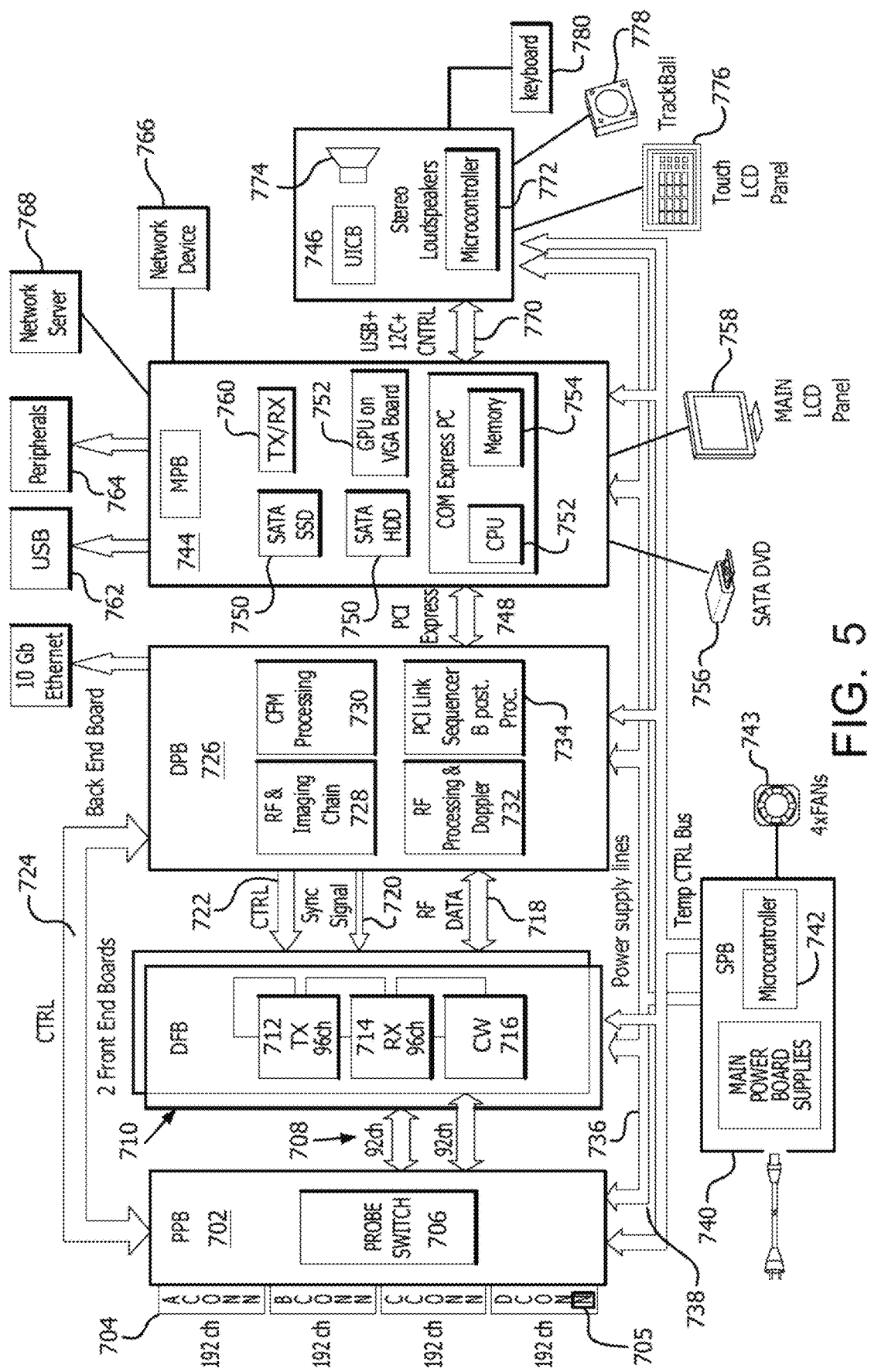
FIG. 5 to 7 illustrates the diagrams of an alternative embodiment of an ultrasound system which is configured by loading and executing specific software the functions of a method and a system according to the present invention.

FIG. 4 is an example of a preferred but non limiting embodiment of the activation and/or deactivation method according to the present invention and which can be carried out by one or more of the embodiments described in the present disclosure.

At step 400 a probe is connected with its communication interface to the corresponding communication interface of an ultrasound system.

At step 410 the ultrasound system by means for example of the selecting circuit of the example of FIG. 1, carries out the probe recognition step by reading and/or receiving the Probe identification code and/or the values of the setting parameters for the ultrasound scanner for driving the probe. At step 420, which can be also an optional step, the Probe identification code and/or the values of the setting parameters for the ultrasound scanner for driving the probe may be loaded in a memory of the ultrasound scanner. This step is optional since as disclosed above in an embodiment, the values of the setting parameters for the ultrasound scanner for driving the probe may be already stored in a database in a memory of the ultrasound system or may not. In both cases the said setting parameters for the ultrasound scanner for driving the probe may be loaded also in parallel in a transitory memory in a ready to use condition for being loaded by the control processors of the ultrasound system when the probe is activated.

At step 430 the ultrasound system starts reading and/or receiving the probe motion and/or orientation signals from the sensor or sensors provided on the probe and starts further to compare the said signals with the reference signal or signals determined for example according to the embodiment of FIG. 3 and or other variant embodiments disclosed above or also combinations thereof.

The results of the comparison with the reference system may indicate that the probe has been displaced according to a characteristic probe displacement for using the probe as indicated at step 440 or that the probe is stationary or at rest or is oriented in a certain way representing a condition of use as indicated at step 441.

If indicated by the steps 442 and 443 one of the two conditions, namely that the probe has been displaced according to a characteristic probe displacement for using the probe as indicated at step 440 or that the probe is oriented in a certain way representing a condition of use as indicated at step 441 the methods provides for the step 450 of generating a probe activation signal driving the ultrasound control processor to load the setting parameters of the corresponding probe being considered in use followed by step 460 of activating the communication of the rx/tx interface of the probe with the transmit beam excitation channels and with the receive beam processing channels and/or in general with the processing hardware of the ultrasound system which drives the probe and processes the received signals till to the generation and display of an image therefrom.

On the contrary, if as indicated by the steps 442 and 443, the result of the two comparisons provides the following result that the probe has not been displaced and/or that the displacement of the probe is not according to a characteristic probe displacement for using the probe and at the same time that probe is stationary or at rest or is oriented in a certain way corresponding to a not in use or rest condition of the probe, the following steps are carried out:

As indicated by 470 the probe is maintained inactive or is switched to inactive by cutting the communication between the Rx/Tx communication interface and the transmit beams excitation channels and the receive beams processing channels of the corresponding probe or generally speaking with the processing circuit of the ultrasound system which drives the probe and processes the received signals until the generation and display of an image therefrom.

This step may be followed by the step 480 which prevent loading of the setting parameters of the ultrasound scanner for the corresponding probe by the ultrasound scanner control processors or changes the setting parameters with the one probe which is considered active according to the carrying out of the above steps for this further probe.

FIG. 4 illustrates a block diagram of an ultrasound system formed in accordance with an alternative embodiment. The system of FIG. 4 implements the operations described herein in connection with various embodiments. By way of example, one or more circuits/processors within the system implement the operations of any processes illustrated in connection with the figures and/or described herein.

In particular any processor may be provided in combination with a software which comprises the instructions for carrying out at least one part of the functions and steps of the present method and which software is loaded and executed by the said processor/processors according to the embodiment already disclosed with reference to FIGS. 1 to 4. In particular the functional hardware/software blocks relating to the selecting circuit 130, to the communication interfaces of the ultrasound system and of the probes 117-1, 117-2, 117.*n* 160-1, 160-2, 160-*n*, and the functional units of probe and ultrasound system of the embodiment according to FIG. 2 may be in the form of generic processing units in which a specific software which comprises the instructions for carrying out the functions according to the embodiments of FIGS. 1 to 4 are loaded and which software is executed by the said generic hardware.

In relation to the specific embodiment, the system includes a probe interconnect board 702 that includes one or more probe connection ports 704. The connection ports 704 may support various numbers of signal channels (e.g., 128, 192, 256, etc.). The connector ports 704 may be configured to be used with different types of probe arrays (e.g., phased array, linear array, curved array, 1D, 1.25D, 1.5D, 1.75D, 2D array, etc.). The probes may be configured for different types of applications, such as abdominal, cardiac, maternity, gynecological, urological and cerebrovascular examination, breast examination and the like.

One or more of the connection ports 704 may support acquisition of 2D image data and/or one or more of the connection ports 704 may support 3D image data. By way of example only, the 3D image data may be acquired through physical movement (e.g., mechanically sweeping or physician movement) of the probe and/or by a probe that electrically or mechanically steers the transducer array.

The probe interconnect board (PIB) 702 includes a switching circuit 706 to select between the connection ports 704. The switching circuit 706 may be manually managed based on user inputs. For example, a user may designate a connection port 704 by selecting a button, switch or other input on the system. Optionally, the user may select a connection port 704 by entering a selection through a user interface on the system.

Optionally, the switching circuit 706 may automatically switch to one of the connection ports 704 in response to detecting a presence of a mating connection of a probe. For example, the switching circuit 706 may receive a "connect" signal indicating that a probe has been connected to a select one of the connection ports 704. The connect signal may be generated by the probe when power is initially supplied to the probe when coupled to the connection port 704. Additionally or alternatively, each connection port 704 may include a sensor 705 that detects when a mating connection on a cable of a probe has been interconnected with the corresponding connection port 704. The sensor 705 provides a connect signal to the switching circuit 706, and in response thereto, the switching circuit 706 couples the corresponding connection port 704 to PIB outputs 708. Optionally, the sensor 705 may be constructed as a circuit with contacts provided at the connection ports 704. The circuit remains open when no mating connected is joined to the corresponding connection port 704. The circuit is closed when the mating connector of a probe is joined to the connection port 704. The switching circuit may be also driven by a software processing signals coming from motion and/or orientation sensors associated to a probe and which signals are analyzed for determining the motion and orientation status of each probe connected to the board and for activating the switching such that the probe is connected to the processing channels of the processing board 724. The switching and the analysis of the motion and/or orientation signals coming from the sensor/sensors on the probe are processed according to one or more of the embodiments disclosed above in relation to the generic features disclosed in the summary of the invention and in the specific embodiments of FIGS. 1 to 4.

A control line 724 conveys control signals between the probe interconnection board 702 and a digital processing board 726. A power supply line 736 provides power from a power supply 740 to the various components of the system, including but not limited to, the probe interconnection board (PIB) 702, digital front end boards (DFB) 710, digital processing board (DPB) 726, the master processing board (M PB) 744, and a user interface control board (UI CB) 746. A temporary control bus 738 interconnects, and provides temporary control signals between, the power supply 740 and the boards 702, 710, 726, 744 and 746. The power supply 740 includes a cable to be coupled to an external AC power supply. Optionally, the power supply 740 may include one or more power storage devices (e.g. batteries) that provide power when the AC power supply is interrupted or disconnected. The power supply 740 includes a controller 742 that manages operation of the power supply 740 including operation of the storage devices.

Additionally or alternatively, the power supply 740 may include alternative power sources, such as solar panels and the like. One or more fans 743 are coupled to the power supply 740 and are managed by the controller 742 to be turned on and off based on operating parameters (e.g. temperature) of the various circuit boards and electronic components within the overall system (e.g. to prevent overheating of the various electronics).

The digital front-end boards 710 providing analog interface to and from probes connected to the probe interconnection board 702. The DFB 710 also provides pulse or control and drive signals, manages analog gains, includes analog to digital converters in connection with each receive channel, provides transmit beamforming management and receive beamforming management and vector composition (associated with focusing during receive operations).

The digital front end boards 710 include transmit driver circuits 712 that generate transmit signals that are passed over corresponding channels to the corresponding transducers in connection with ultrasound transmit firing operations. The transmit driver circuits 712 provide pulse or control for each drive signal and transmit beamforming management to steer firing operations to points of interest within the region of interest. By way of example, a separate transmit driver circuits 712 may be provided in connection with each individual channel, or a common transmit driver circuits 712 may be utilized to drive multiple channels. The transmit driver circuits 712 cooperate to focus transmit beams to one or more select points within the region of interest. The transmit driver circuits 712 may implement single line transmit, encoded firing sequences, multiline transmitter operations, generation of shear wave inducing ultrasound beams as well as other forms of ultrasound transmission techniques.

The digital front end boards 710 include receive beamformer circuits 714 that received echo/receive signals and perform various analog and digital processing thereon, as well as phase shifting, time delaying and other operations in connection with beamforming. The beam former circuits 714 may implement various types of beamforming, such as single-line acquisition, multiline acquisition as well as other ultrasound beamforming techniques.

The digital front end boards 716 include continuous wave Doppler processing circuits 716 configured to perform continuous wave Doppler processing upon received echo signals. Optionally, the continuous wave Doppler circuits 716 may also generate continuous wave Doppler transmit signals.

The digital front-end boards 710 are coupled to the digital processing board 726 through various buses and control lines, such as control lines 722, synchronization lines 720 and one or more data bus 718. The control lines 722 and synchronization lines 720 provide control information and data, as well as synchronization signals, to the transmit drive circuits 712, receive beamforming circuits 714 and continuous wave Doppler circuits 716. The data bus 718 conveys RF ultrasound data from the digital front-end boards 710 to the digital processing board 726. Optionally, the digital front end boards 710 may convert the RF ultrasound data to I,Q data pairs which are then passed to the digital processing board 726.

The digital processing board 726 includes an RF and imaging module 728, a color flow processing module 730, an RF processing and Doppler module 732 and a PCI link module 734. The digital processing board 726 performs RF filtering and processing, processing of black and white image information, processing in connection with color flow, Doppler mode processing (e.g. in connection with polls wise and continuous wave Doppler). The digital processing board 726 also provides image filtering (e.g. speckle reduction) and scanner timing control. The digital processing board 726 may include other modules based upon the ultrasound image processing functionality afforded by the system.

The modules 728-734 comprise one or more processors, DSPs, and/or FPGAs, and memory storing program instructions to direct the processors, DSPs, and/or FPGAs to perform various ultrasound image processing operations. The RF and imaging module 728 performs various ultrasound related imaging, such as B mode related image processing of the RF data. The RF processing and Doppler module 732 convert incoming RF data to I,Q data pairs, and performs Doppler related processing on the I, Q data pairs. Optionally, the imaging module 728 may perform B mode related image processing upon I, Q data pairs. The CFM processing module 730 performs color flow related image processing upon the ultrasound RF data and/or the I, Q data pairs. The PCI link 734 manages transfer of ultrasound data, control data and other information, over a PCI express bus 748, between the digital processing board 726 and the master processing board 744.

The master processing board 744 includes memory 750 (e.g. serial ATA solid-state devices, serial ATA hard disk drives, etc.), a VGA board 752 that includes one or more graphic processing unit (GPUs), one or more transceivers 760 one or more CPUs 752 and memory 754. The master processing board (also referred to as a PC board) provides user interface management, scan conversion and cine loop management. The master processing board 744 may be connected to one or more external devices, such as a DVD player 756, and one or more displays 758. The master processing board includes communications interfaces, such as one or more USB ports 762 and one or more ports 764 configured to be coupled to peripheral devices. The master processing board 744 is configured to maintain communication with various types of network devices 766 and various network servers 768, such as over wireless links through the transceiver 760 and/or through a network connection (e.g. via USB connector 762 and/or peripheral connector 764).

The network devices 766 may represent portable or desktop devices, such as smart phones, personal digital assistants, tablet devices, laptop computers, desktop computers, smart watches, ECG monitors, patient monitors, and the like. The master processing board 744 conveys ultrasound images, ultrasound data, patient data and other information and content to the network devices for presentation to the user. The master processing board 744 receives, from the network devices 766, inputs, requests, data entry and the like.

The network server 768 may represent part of a medical network, such as a hospital, a healthcare network, a third-party healthcare service provider, a medical equipment maintenance service, a medical equipment manufacturer, a government healthcare service and the like. The communications link to the network server 768 may be over the Internet, a private intranet, a local area network, a wide-area network, and the like.

The master processing board 744 is connected, via a communications link 770 with a user interface control board 746. The communications link 770 conveys data and information between the user interface and the master processing board 744. The user interface control board 746 includes one or more processors 772, one or more audio/video components 774 (e.g. speakers, a display, etc.). The user interface control board 746 is coupled to one or more user interface input/output devices, such as an LCD touch panel 776, a trackball 778, a keyboard 780 and the like. The processor 772 manages operation of the LCD touch panel 776, as well as collecting user inputs via the touch panel 776, trackball 778 and keyboard 780, where such user inputs are conveyed to the master processing board 744 in connection with implementing embodiments herein.

Figure 6:
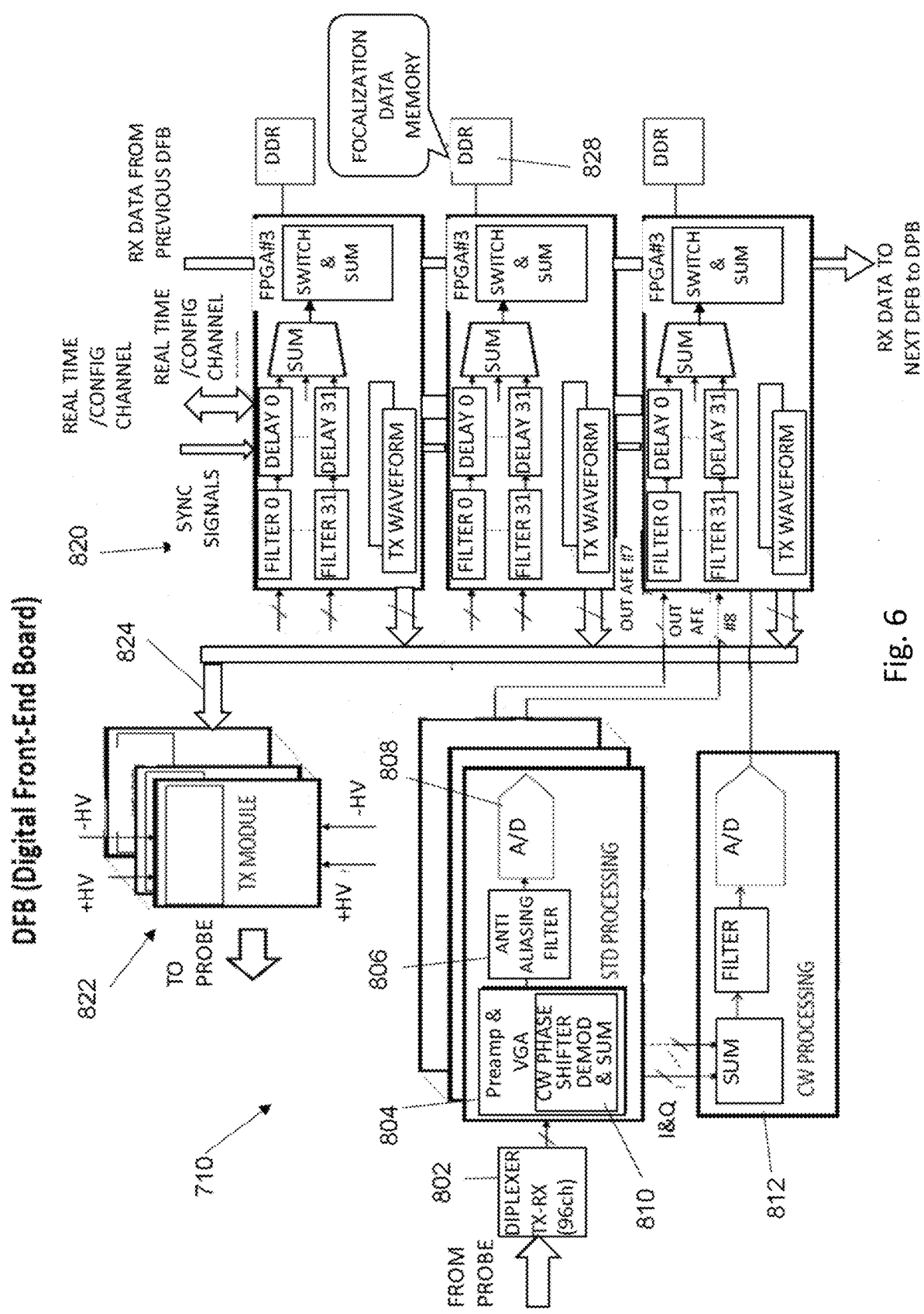
Figure 7:
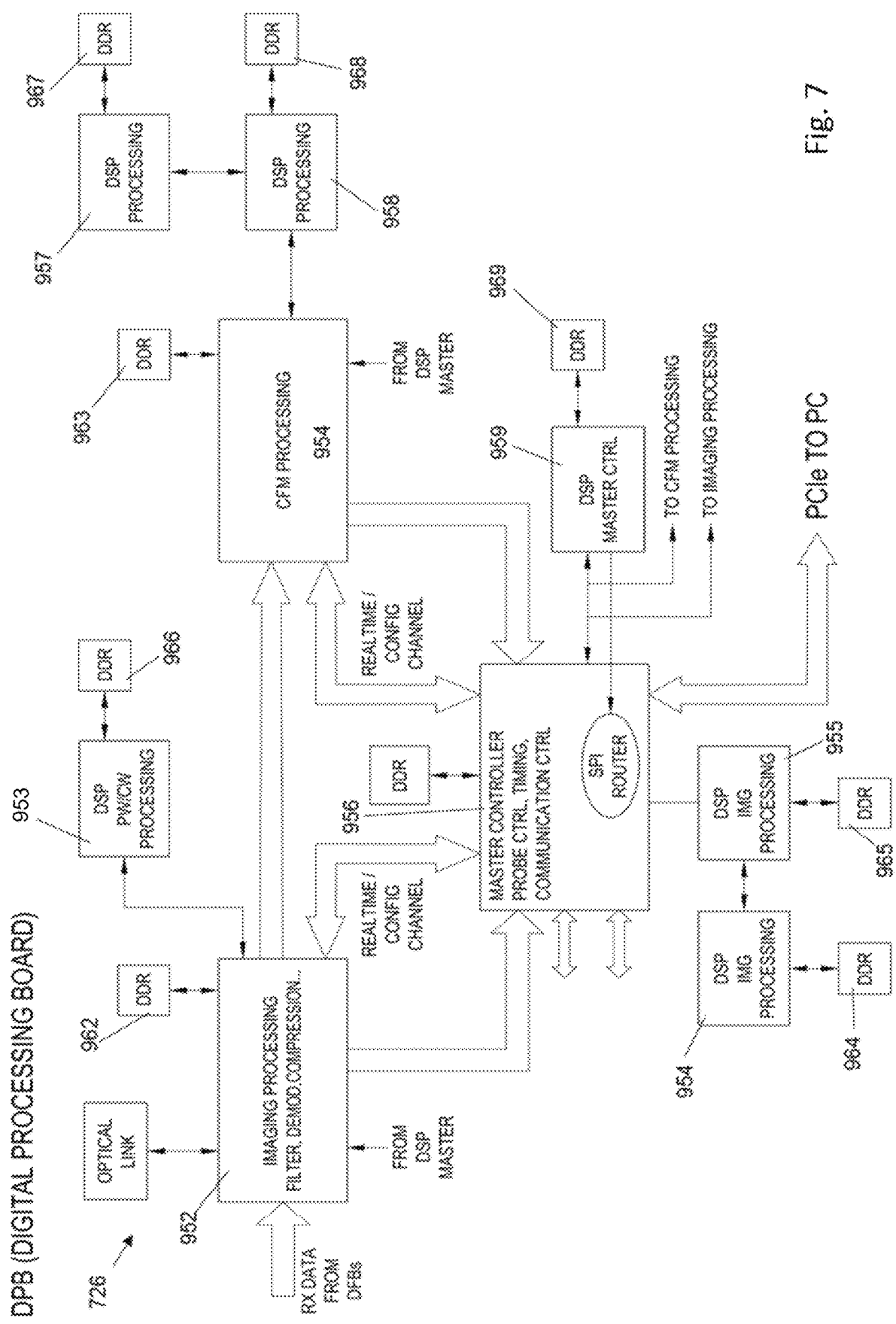

FIG. 6 illustrates a block diagram of a portion of the digital front-end boards 710 formed in accordance with embodiments herein. A group of diplexers 802 receive the ultrasound signals for the individual channels over the PIB output 808. The ultrasound signals are passed along a standard processing circuit 805 or to a continuous wave processing circuit 812, based upon the type of probing utilized. When processed by the standard processing circuit 805, a preamplifier and variable gain amplifier 804 process the incoming ultrasound receive signals that are then provided to an anti-aliasing filter 806 which performs anti-aliasing filtering. The output thereof is provided to an A/D converter 808 that digitizes the incoming analog ultrasound receive signals. When a continuous wave (CW) probe is utilized, the signals therefrom are provided to a continuous wave phase shifter, demodulator and summer 810 which converts the analog RF receive signals to I,Q data pairs. The CW I,Q data pairs are summed, filtered and digitized by a continuous wave processing circuit 812. Outputs from the standard or continuous wave processing circuits 805, 812 are then passed to beam forming circuits 820 which utilize one or more FPGAs to perform filtering, delaying and summing the incoming digitized receive signals before passing the RF data to the digital processing board 826 (FIG. 7). The FPGAs receive focalization data from memories 828. The focalization data is utilized to manage the filters, delays and summing operations performed by the FPGAs in connection with beamforming. The being formed RF data is passed between the beamforming circuits 820 and ultimately to the digital processing board 726.

The digital front-end boards 710 also include transmit modules 822 that provide transmit drive signals to corresponding transducers of the ultrasound probe. The beamforming circuits 820 include memory that stores transmit waveforms. The transmit modules 822 receive transmit waveforms over line 824 from the beamforming circuits 820.

FIG. 7 illustrates a block diagram of the digital processing board 726 implemented in accordance with embodiments herein. The digital processing board 726 includes various processors 952-959 to perform different operations under the control of program instructions saved within corresponding memories see 962-969. A master controller 956 manages operation of the digital processing board 726 and the processors 952-959. By way of example, one or more processors as the 952 may perform filtering, the modulation, compression and other operations, while another processor 953 performs color flow processing. The master controller provides probe control signals, timing control signals, communications control and the like. The master controller 956 provides real-time configuration information and synchronization signals in connection with each channel to the digital front-end board 710.

It should be clearly understood that the various arrangements and processes broadly described and illustrated with respect to the figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The controller may include any processor-based or microprocessor-based system including systems using microcontrollers, reduced instruction set computers (RISC), application specific integrated circuitry (ASICs), field-programmable gate arrays (FPGAs), logic circuitry, and any other circuit or processor capable of executing the functions described herein. When processor-based, the controller executes program instructions stored in memory to perform the corresponding operations. Additionally or alternatively, the controllers and the controller device may represent circuitry that may be implemented as hardware. The above examples are exemplary only, and are thus not intended to limit in any way the definition and/or meaning of the term "controller."

Optionally, aspects of the processes described herein may be performed over one or more networks one a network server. The network may support communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C # or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

The invention claimed is:

1. A method for automatic detection of a probe selected for use by a user without manual commands comprising:
monitoring operational status of the probe as one of an active probe for ultrasound image acquisition scans and an inactive probe by discriminating between the probe not in use and the probe in use by sensing motion and orientation in space of the probe;
using the motion of the probe and the orientation in space of the probe as criteria for monitoring the operative status of the probe to determine when the probe is in use and when the probe is in not in use corresponding to a stand-by or parking position at a probe stand of an ultrasound system by
comparing sensed motion signals of the probe with one or more reference signals that correspond to characteristic movements of the probe to determine when a motion threshold is satisfied that indicates the probe is in use, and
comparing sensed orientation signals of the probe with one or more reference signals that correspond to characteristic orientation of the probe to determine when an orientation threshold is satisfied that indicates the probe is in use;
operating the probe as an active probe when at least one of the sensed motion signals and the sensed orientation signals indicate the probe is in use; and
operating the probe as an inactive probe when both of the sensed motion signals and the sensed orientation signals indicate the probe is not in use.

2. A method according to claim 1, wherein the probe is provided with motion sensors, the motion sensors generating different signals as a function of the motion of the probe.

3. A method according to claim 2, wherein the comparing sensed motion signals comprises differentiating between a null signal generated when the probe is not moving and a motion signal different from the null signal generated when the probe is moving, and the null signal and the motion signal being used as control signals of a probe activation selector which automatically drives a selection circuit of an ultrasound scanner, the selection circuit being configured to set the corresponding probe as the active probe for the ultrasound image acquisition scans.

4. A method according to claim 2, further comprising adding to the different signals generated as a function of the motion of the probe a probe identification code and optionally a data record comprising at least part of the probe configuration parameters necessary for correctly driving the probe for carrying out ultrasound imaging scans.

5. A method according to claim 4, comprising two alternative operations that are selectable when the probe is being connected to an ultrasound system, the alternative operations being:
storing the data record and transmitting the probe configuration parameters of the data record to the ultrasound system with or without the identification code;
storing the data record in a memory of the ultrasound system and loading by the ultrasound system the probe configuration parameters when the probe is connected to the ultrasound system and the probe identification code is sent and/or is read by the ultrasound system.

6. A method according to claim 1, comprising sensing the orientation in space of the probe and using the orientation in space of the probe to determine if the probe is in use, or the probe is not in use such as when the probe is in the stand-by or parking position at the probe stand of the ultrasound system.

7. A method according to claim 1, wherein the operative status is determined by identifying a change from a characteristic orientation the probe has when at the probe stand and a characteristic orientation the probe has when ready to be used for carrying out an imaging scan.

8. Ultrasound system comprising:
at least one ultrasound probe connected to a probe communication interface of the ultrasound system; and
a processing unit configured to
monitor operational status of the probe as one of an active probe for ultrasound image acquisition scans and an inactive probe by discriminating between the probe not in use and the probe in use by sensing motion and orientation in space of the probe;
use the motion of the probe and the orientation in space of the probe as criteria for monitoring the operative status of the probe to determine when the probe is in use and when the probe is in not in use corresponding to a stand-by or parking position at a probe stand of an ultrasound system by
comparing sensed motion signals of the probe with one or more reference signals that correspond to characteristic movements of the probe to determine when a motion threshold is satisfied that indicates the probe is in use, and
comparing sensed orientation signals of the probe with one or more reference signals that correspond to characteristic orientation of the probe to determine when an orientation threshold is satisfied that indicates the probe is in use;
operate the probe as an active probe when at least one of the sensed motion signals and the sensed orientation signals indicate the probe is in use, and
operate the probe as an inactive probe when both of the sensed motion signals and the sensed orientation signals indicate the probe is not in use.

9. Ultrasound system according to claim 8, comprising a probe selection circuit having an input for the signals indicating the activation condition of the probe, the processing unit being configured to generate a probe activation signal or a probe deactivation signal as a function of the signals indicating the activation condition of the probe.

10. Ultrasound system according to claim 9, wherein the probe selection circuit is provided in combination with signaling elements generating visual information relating to one or more of the following conditions: probes connected to the ultrasound system and being activable for use; probe currently activated.

11. Ultrasound system according to claim 9, further comprising a database of data records comprising probe configuration parameters for driving the probe, the database being stored in a probe memory and the data record for each probe further comprising a probe identification code for the corresponding probe, the probe selection circuit being configured to receive the identification code from a probe connected to the ultrasound system and automatically address the data record of the probe corresponding to said probe identification code, the probe selection circuit being configured to automatically connect to the ultrasound system control processor and transmit to said control processor the probe configuration parameters corresponding to the probe identification code for configuring the ultrasound system to correctly drive the probe.

12. Ultrasound system according to claim 9, wherein the probe selection circuit is configured to generate a list of different probes connected to the ultrasound system and to address the data record corresponding to the probe identification code of the probe set in the active status based on the signals indicating the activation condition of the probe and the probe selection circuit is configured to transmit the probe configuration parameters relating to the probe set in the active status to the ultrasound system control processor for correct configuration of the system for driving the probe.

13. Ultrasound system according to claim 8 comprising one or more sensors measuring the motion and/or orientation in space of the probe, the one or more sensors having an output for signals indicating the motion and/or orientation in space of the probe, i.e. if the probe stands still in a parking position or if the probe is subject to displacements, the signals being predetermined to represent an activation condition of the probe.

14. Ultrasound system according to claim 13, wherein the output of motion and orientation sensors are combined to provide the signals representing the activation condition of the probe.

15. Ultrasound system according to claim 13, comprising a memory storing a probe identification code which identification code is characteristic for the probe and a combination unit to which the memory and the one or more sensors are connected, the combination unit being configured to combine the probe identification code and the signal indicating the activation condition of the probe.

16. Ultrasound system according to claim 15, wherein a memory is provided in which configuration parameters characteristic for the probe are stored and which probe configuration parameters are configured according to a predetermined data record in order to be readable by a receiving unit, the combination unit being configured to combine the probe configuration parameters of the data record, the identification code of the probe and optionally the signals indicating the activation condition of the probe.

\* \* \* \* \*